United States Patent
Petropoulos et al.

(10) Patent No.: US 12,055,610 B2
(45) Date of Patent: Aug. 6, 2024

(54) SINGLE SHIM COIL DESIGN FOR $B_0$ SHIMMING

(71) Applicant: Quality Electrodynamics, LLC, Mayfield Village, OH (US)

(72) Inventors: Labros Petropoulos, Maple Grove, MN (US); Xiaoyu Yang, Indiana, PA (US); Hiroyuki Fujita, Highland Heights, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 521 days.

(21) Appl. No.: 17/166,057

(22) Filed: Feb. 3, 2021

(65) Prior Publication Data

US 2021/0239777 A1 Aug. 5, 2021

Related U.S. Application Data

(60) Provisional application No. 62/969,215, filed on Feb. 3, 2020.

(51) Int. Cl.
*G01R 33/3875* (2006.01)
*A61B 5/00* (2006.01)
(Continued)

(52) U.S. Cl.
CPC .......... *G01R 33/3875* (2013.01); *A61B 5/055* (2013.01); *A61B 5/4585* (2013.01); *G01R 33/34084* (2013.01); *G01R 33/543* (2013.01)

(58) Field of Classification Search
CPC .......... G01R 33/3875; G01R 33/34084; G01R 33/543; A61B 5/055; A61B 5/4585
See application file for complete search history.

(56) References Cited

U.S. PATENT DOCUMENTS 5,977,771 A  11/1999  Petropoulos
6,262,576 B1  7/2001  Petropoulos
(Continued)

OTHER PUBLICATIONS

Hu et al. "Shim Coil Set for NMR Using a Novel Target Field Method Based on Trigonometric Series" IEEE Transactions on Applied Superconductivity, vol. 24, No. 3, Jun. 2014. Published on Nov. 28, 2013.

(Continued)

*Primary Examiner* — Patrick Fernandes
*Assistant Examiner* — Nicholas A Robinson
(74) *Attorney, Agent, or Firm* — Eschweiler & Potashnik, LLC

(57) ABSTRACT

Various embodiments of the present disclosure are directed towards a magnetic resonance imaging (MRI) knee coil comprising a local shim coil. The local shim coil is disposed in a housing of the MRI knee coil. An electromagnetic coil is also disposed in the housing and spaced from the local shim coil. The local shim coil comprises one or more conductors. Each of the conductors of the local shim coil are disposed on a semi-cylindrical surface, and the semi-cylindrical surface extends laterally from a first side of the housing to a second side of the housing. The local shim coil is configured to generate a local shimming magnetic field that reduces a localized magnetic field inhomogeneity caused by a susceptibility artifact disposed in a knee of a patient.

20 Claims, 8 Drawing Sheets

(51) Int. Cl.
  *A61B 5/055* (2006.01)
  *G01R 33/34* (2006.01)
  *G01R 33/54* (2006.01)

(56) References Cited

U.S. PATENT DOCUMENTS

| | | | |
|---|---|---|---|
| 6,342,787 B1 * | 1/2002 | Petropoulos | G01R 33/3875 |
| | | | 324/319 |
| 6,788,057 B1 | 9/2004 | Petropoulos et al. | |
| 9,329,247 B2 | 5/2016 | Biber | |
| 9,360,541 B2 | 6/2016 | Biber | |
| 2012/0274326 A1 * | 11/2012 | Lee | G01R 33/3415 |
| | | | 324/318 |
| 2015/0054510 A1 * | 2/2015 | Biber | A61B 5/055 |
| | | | 324/322 |
| 2016/0334479 A1 * | 11/2016 | Poole | G01R 33/34007 |
| 2018/0081004 A1 * | 3/2018 | Yang | H03F 3/2175 |
| 2018/0275234 A1 * | 9/2018 | Han | A61B 5/459 |
| 2018/0313918 A1 * | 11/2018 | Yang | G01R 33/3415 |

OTHER PUBLICATIONS

Martens et al. "Insertable biplanar gradient coils for magnetic resonance imaging" Review of Scientific Instruments 62, 2639 (1991); doi: 10.1063/1.1142245. Published on Jul. 28, 1991.

Hu et al. "Shim Coil Set for an Open Biplanar MRI System Using an Inverse Boundary Element Method" IEEE Transactions on Applied Superconductivity, vol. 26, No. 7, Oct. 2016. Published on Aug. 31, 2016.

Turner, Robert. "Minimum inductance coils" Journal of Physics E: Scientific Instruments, 21 948, published on May 16, 1988.

* cited by examiner

SINGLE SHIM COIL DESIGN FOR $B_0$ SHIMMING

REFERENCE TO RELATED APPLICATION

This application claims the benefit of U.S. Provisional Application No. 62/969,215, filed on Feb. 3, 2020, the contents of which are incorporated by reference in their entirety.

BACKGROUND

The target field method is a theory to produce a specified magnetic field with the minimum possible stored magnetic energy (controlling the current density). It is still being exploited in typical shim coil designs for magnetic resonance imaging (MRI) and nuclear magnetic resonance (NMR) systems today. However, these typical shim coils, like the ones fitted in a MRI scanner, are low-order spherical harmonic (SH) shims that are not designed to eliminate (or reduce) a spatially localized $B_0$ offset. For example, a small void under (posterior) the patella can result in a strong and localized magnetic field distortion due to a susceptibility difference between air and tissue (e.g., adipose tissue). This localized magnetic field inhomogeneity cannot be addressed by low-order SH shims. Rather, these SH shims are designed to eliminate spatially globalized magnetic field distortions (e.g., distortions across the entire bore of the MRI scanner).

In existing approaches that have attempted to eliminate localized magnetic field distortions, a local shim coil is placed at a position of, for example, a head radio frequency (RF) coil by trial and error. Thus, the local shim coil is placed at the position without any regard to the position of the local shim coil relative to a localized magnetic field inhomogeneity. In other words, a justified calculation is not carried out to determine the precise location of the local shim coil in relation to the localized magnetic field inhomogeneity to ensure the local shim coil eliminates (or reduces) the localized magnetic field inhomogeneity. As such, the local shim coil generates an arbitrary magnetic field that does not effectively eliminate (or reduce) the localized magnetic field inhomogeneity.

Further, in such existing approaches, a shape of the local shim coil is a two-dimensional loop. This simple two-dimensional loop shape is not tailored to eliminate (or reduce) the localized magnetic field inhomogeneity. Moreover, in such existing approaches, a current of the local shim coil is calculated by trial and error. As such, the shape (e.g., the two-dimensional loop) of the local shim coil and the trial and error calculation of the current of the local shim coil may not effectively reduce the localized magnetic field inhomogeneity. For example, the local shim coil may not effectively reduce the localized magnetic field inhomogeneity due to the shape of the local shim coil (and/or the trial and error calculation of the current) not being able to generate a complex magnetic field that eliminates the localized magnetic field inhomogeneity.

In another example, current patterns may be generated based on an inverse method for magnetic fields that have a symmetric behavior around a large volume. In such embodiments, a Green's function may be defined for symmetric fields and structures, and the Green's function may be applied solely to applications that have symmetry and such a Green's function may not exist for non-symmetric configurations. Such Green's function is used for volumetric field generation and may not be used in localized field generation.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1A:
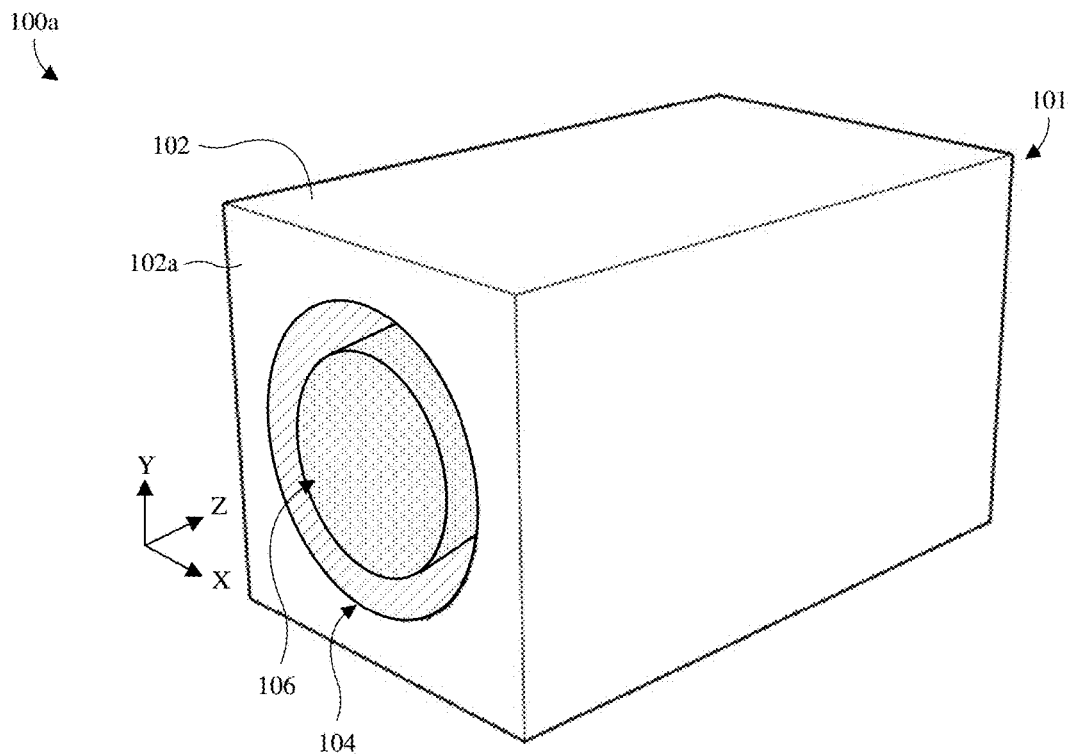
FIGS. 1A-1C illustrate various perspective views of some embodiments of a magnetic resonance imaging (MRI) knee coil comprising a local shim coil that reduces a localized magnetic field inhomogeneity.

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Various embodiments of the present disclosure are directed toward a magnetic resonance imaging (MRI) coil comprising a local shim coil that is configured to accurately eliminate (or reduce) a highly localized magnetic field inhomogeneity. For example, the MRI coil may be a MRI knee coil comprising the local shim coil that is configured to eliminate (or reduce) a highly localized magnetic field inhomogeneity caused by a small void under (posterior) the patella. This small void under the patella is present when the knee is bent (flexion) at an angle (e.g., greater than or equal to about five degrees).

The local shim coil comprises one or more conductors. The conductors of the local shim coil are bound to lie on a specific surface. For example, in some embodiments, each of the conductors of the local shim coil are disposed on a semi-cylindrical surface. Unlike other shim coils/techniques (e.g., low-order SH shimming, rudimentary local shim coils, etc.), the local shim coil of the present disclosure is capable of eliminating (or reducing) the localized magnetic field inhomogeneity due to the local shim coil being configured to output a local shimming magnetic field that is counter to (e.g., equal to and opposite) the localized magnetic field inhomogeneity (described in more detail hereinafter). Therefore, because the local shim coil eliminates or reduces the localized magnetic field inhomogeneity caused by the small void under (posterior) the patella, patient comfort during imaging may be improved (e.g., some injured patients experience less pain when their knee is bent during the MRI scan). In addition, the local shim coil may improve image quality (e.g., by eliminating (or reducing) the negative effects that the localized magnetic field inhomogeneity has on image quality).

Figure 1B:
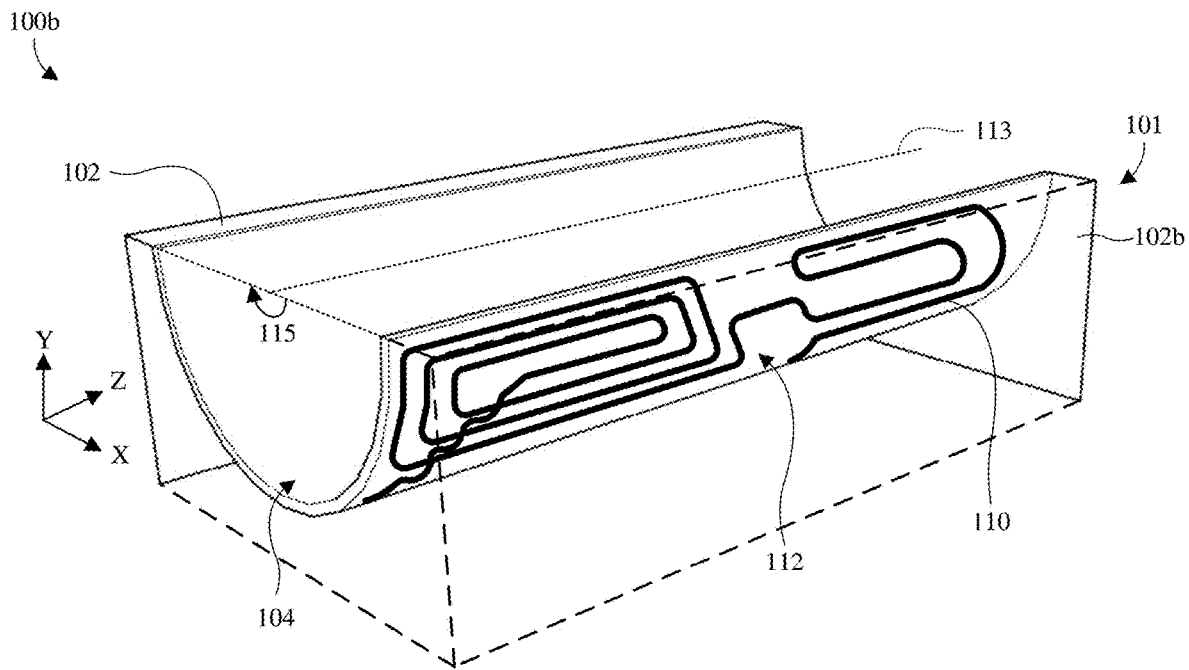
Figure 1C:
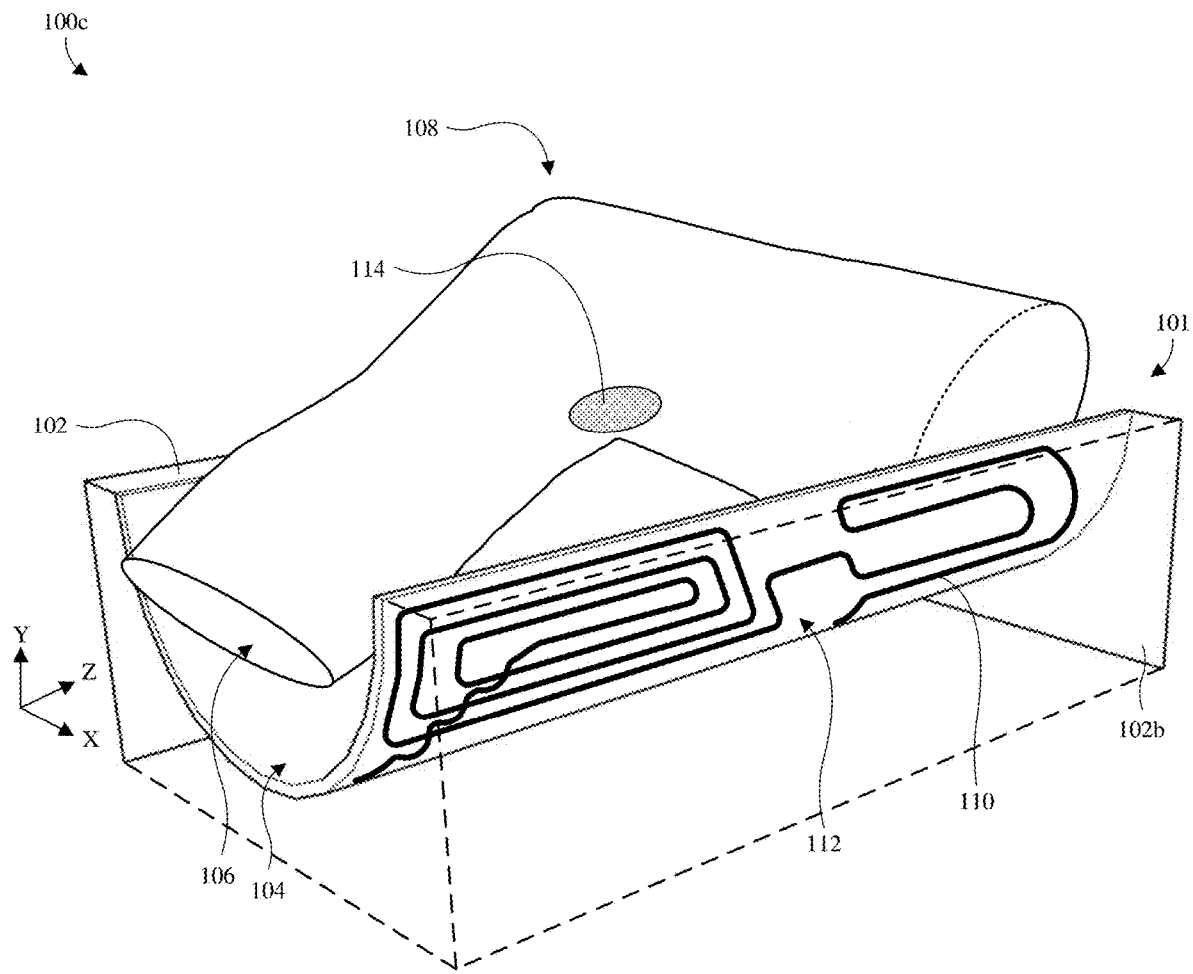

FIGS. 1A-1C illustrate various perspective views 100a-100c of some embodiments of a magnetic resonance imaging (MRI) knee coil 101 comprising a local shim coil 110 that reduces a localized magnetic field inhomogeneity. FIG. 1A illustrates a perspective view 100a of the MRI knee coil 101 with a constructed housing 102 (e.g., no outer panels removed from the housing 102). FIG. 1B illustrates a perspective view 100b in which the MRI knee coil 101 is partially deconstructed (e.g., some outer panels are illustrated in phantom (by dotted lines) and an upper portion of the housing 102 is removed). FIG. 1C illustrates a perspective view 100c in which the MRI knee coil 101 is partially deconstructed and the bent knee 108 of a patient 106 is disposed within the opening 104 (e.g., at a location in which a patient's knee is positioned during an MRI scan of the knee).

As shown in the perspective views 100a-100c of FIGS. 1A-1C, a MRI knee coil 101 is provided. The MRI knee coil 101 comprise a housing 102. In some embodiments, the housing 102 is or comprises, for example, plastic, resin, glass fiber, or the like.

The housing 102 has an opening 104 (e.g., a bore). The opening 104 extends laterally (along the z-axis) through the housing 102 from a first side 102a of the housing 102 to a second side 102b of the housing 102 opposite the first side 102a of the housing 102, such that a patient 106 is capable of positioning their knee 108 within the opening 104. More specifically, the knee 108 of the patient is positioned between the first side 102a and the second side 102b of the housing 102.

While the perspective view 100a of FIG. 1A illustrates the opening 104 extending through the housing 102 such that portions of the housing 102 surround a top, bottom, left side, and right side of the opening 104, it will be appreciated that other openings are amenable. For example, the housing 102 may be C-shaped, such that portions of the housing 102 only surround three sides of the opening 104 (e.g., only surround the top, bottom, and left side, or some other combination). In other embodiments, the housing 102 may be such that only two sides of the opening 104 (e.g., the top and bottom of the opening 104) are covered by the housing 102.

In yet other embodiments, the housing 102 may comprise a bottom portion and a top portion (or a left side portion and a right side portion). The bottom portion and the top portion of the housing 102 are designed so that the top portion may be removed (or hinged) from the bottom portion (e.g., to allow the patient's knee 108 to be positioned over the bottom portion) and attached to the bottom portion of the housing 102 (e.g., to secure the top portion over the patient's knee 108 after the knee 108 is positioned over the bottom portion). In such embodiments, certain coils of the MRI knee coil 101 (e.g., transmit coil and/or receive coil) may then surround the patient's knee 108 (e.g., surround the top (anterior), bottom (posterior), left side (medial), and right side (lateral)) by having an upper portion of such coils couple to bottom portions of such coils. Image quality may be improved in such embodiments due to the certain coils wrapping fully around the patient's knee 108.

The MRI knee coil 101 comprises a local shim coil 110. The local shim coil 110 is defined by one or more conductors (e.g., copper wire, coaxial cable, copper sheets, silver wire, conductive traces on a flexible printed circuit board (PCB), printed conductors (e.g., screen-printed coils), etc.). The local shim coil 110 is bound to lie on a specific surface. In some embodiments, as shown in the perspective views 100b-100c of FIGS. 1B-1C, the local shim coil 110 is bound to a semi-cylindrical surface 112. In other words, the local shim coil 110 is disposed on the semi-cylindrical surface 112. In some embodiments, as shown in the perspective views 100b-100c of FIGS. 1B-1C, the semi-cylindrical surface 112 is a portion of the housing 102, and the local shim coil 110 is affixed to the portion of the housing 102. However, it will be appreciated that the local shim coil 110 can be affixed to some other structure (e.g., a former) within the housing 102 that has the semi-cylindrical surface 112.

The semi-cylindrical surface 112 extends laterally (along the z-axis) from the first side 102a of the housing 102 to the second side 102b of the housing 102. The semi-cylindrical surface 112 arcs around a central axis 113. The central axis 113 extends (along the z-axis) along the center of the semi-cylindrical surface 112 (e.g., the radius of the semi-cylindrical surface 112 is measure from the central axis 113. In some embodiments, the central axis 113 of the local shim coil 110 also corresponds to a central axis of the opening 104.

The semi-cylindrical surface 112 has a central angle 115. The central angle 115 is the angle in which local shim coil 110 arcs around the central axis 113. In other words, the central angle 115 has a vertex at a point along the central axis 113 and sides (e.g., rays of the central angle 115) that are radii intersecting the local shim coil 110 at two opposite ends of the local shim coil 110.

The central angle 115 of the local shim coil 110 is between one (1) degree and 360 degrees. In some embodiments, the central angle 115 of the local shim coil 110 is greater than or equal to about five (5) degrees and less than or equal to about 190 degrees. In further embodiments, the central angle 115 of the local shim coil 110 is less than or equal to about 180 degrees (e.g., 7C radians). In yet further embodiments, the central angle 115 of the local shim coil 110 is equal to about 180 degrees or 90 degrees (e.g., π/2 radians). It will be appreciated that the central angle 115 (and other dimensions) are based on a polar coordinate system. However, it will also be appreciated that the coordinate system is not limited to a polar coordinate system. Rather, other coordinate systems are amenable.

As shown in the perspective view 100c of FIG. 1C, when the patient's knee 108 is bent (e.g., flexion of greater than five (5) degrees), a susceptibility artifact 114 is present in the patient's leg. The susceptibility artifact 114 occurs naturally in the human knee due to the patient 106 bending their knee 108. The size of the susceptibility artifact 114 is about the same size regardless of the anatomy of the patient 106 (e.g., weight, height, etc.). In other words, the susceptibility artifact 114 has a fairly common size from patient to patient.

The susceptibility artifact 114 is due to a difference in the magnetic susceptibilities of the tissues (or lack of tissues) in and around the patient's bent knee 108. For example, when the patient bends their knee 108, a small void (e.g., pocket of air) is created under (posterior) the patella of the patient's knee 108. As a result of this small void, a highly localized $B_0$ field inhomogeneity (e.g., a strong and localized magnetic field distortion) is created due to the susceptibility difference between air and tissue (e.g., adipose tissue adjacent the small void).

Due to the size and location of the susceptibility artifact 114, typical shim coils may not be able to account for the localized magnetic field inhomogeneity. For example, low-order spherical harmonic (SH) shim coils and rudimentary local shim coils are unable to effectively reduce the localized magnetic field inhomogeneity. As such, the localized magnetic field inhomogeneity may degrade the quality of MR images taken at or near the location of the susceptibility artifact 114. In an effort to reduce the negative effects of the susceptibility artifact 114, the patient 106 is often required to maintain an uncomfortable position throughout the MRI scan. For example, the patient 106 is required to keep their knee as straight as possible in a typical MRI knee coil. This is often an uncomfortable and/or impossible position for the patient 106 to maintain during the MRI scan (e.g., due to an injury, anatomical limitations, etc.).

Thus, to improve MR image quality and/or patient comfort during an MRI scan, a local shim coil that is capable of eliminating (or reducing) the localized magnetic field inhomogeneity caused by the susceptibility artifact 114 is desirable. The local shim coil 110 of the MRI knee coil 101 is configured to reduce (or eliminate) the localized magnetic field inhomogeneity caused by the susceptibility artifact 114. In other words, the local shim coil 110 of the MRI knee coil 101 is configured to reduce (or eliminate) the localized magnetic field inhomogeneity caused by the susceptibility artifact 114.

The local shim coil 110 is configured to reduce the localized magnetic field inhomogeneity by extending, at least partially, the target field method and/or the inverse method. To configure the local shim coil 110 to reduce the localized magnetic field inhomogeneity, the current density is restricted to lie on the specific surface in which the local shim coil 110 is bound. For example, as shown in the perspective views 100b-100c of FIGS. 1B-1C, the local shim coil 110 is bound to the semi-cylindrical surface 112.

Thus, the current density is restricted to the semi-cylindrical surface 112. The semi-cylindrical surface 112 is defined by radius a, length 2c, and arc radian $2_{\varphi 0}$. While making sure that the continuity equation and the boundary conditions are satisfied, the two components of the current density can be expressed as a trigonometric series, and may be written as:

$$J_\Phi(\Phi, z) = a\sum_{m=1}^{\infty}\sum_{m=1}^{\infty} j(n,m)\frac{1}{k_n}\sin k_n\left(\Phi - \Phi_0 + \frac{\pi}{2}\right)\cos\frac{1}{l_m}(z-c)$$

$$J_z(\Phi, z) = -\sum_{m=1}^{\infty}\sum_{m=1}^{\infty} j(n,m)\frac{1}{l_m}\cos k_n\left(\Phi - \Phi_0 + \frac{\pi}{2}\right)\sin\frac{1}{l_m}(z-c)$$

$$k_n = \frac{\pi}{2\Phi_0}n,\ l_m = \frac{\pi}{2c}m,\ J_0\left(\Phi = \frac{\pi}{2}\pm\Phi_0, J_z(z=\pm c)=0\right)$$

$J_{100}$ and $J_z$ represent the current densities of the total current distribution for a cylindrical surface. In addition, these current densities can be represented in terms of a series expansion where j(n,m) are the coefficients and the $\cos(k_n(\varphi))$ depict the symmetry of the azimuthal behavior current density and the symmetry along the axial condition. Also, c depicts the axial half length of the cylindrical surface where the current density is set to be zero.

The total magnetic energy E and the field strength $B_Z$ are calculated in their Fourier space and expressed in terms of j(n,m) (see, infra, Eq. (1)). In the target field approach, a Lagrange multiplier technique is utilized to determine the current density that satisfies the constraints of necessary magnetic field with minimum magnetic energy. By taking the variation with respect to j(n,m), the Lagrange multiplier $\lambda_i$ and the current density can be numerically solved by, for example, the following equation:

$$L[j(n,m)] = E - \sum_i \lambda_i\left(B_z(\vec{r_i}) - B_{z,i}\right) \qquad \text{Eq. (1)}$$

L[j (n, m)] is the minimized quantity. $B_{z,i}$ represents the field constraint points. $B_z(\vec{r}_i)$ defines the expression of the magnetic field at the point ($\vec{r}_i$).

Thus, the local shim coil 110 of the MRI knee coil 101 can be configured to reduce the localized magnetic field inhomogeneity caused by the susceptibility artifact 114. For example, the local shim coil 110 is configured to reduce the localized magnetic field inhomogeneity by utilizing the above equations to determine a current density that will generate a local shimming magnetic field that is counter to (e.g., equal in magnitude and opposite in phase) the localized magnetic field inhomogeneity. A wiring configuration utilizing the stream function methodology of the local shim coil 110 (e.g., the specific layout (e.g., loops, turns, length of wire, etc.) of the conductors of the local shim coil 110), which is bound to the semi-cylindrical surface 112, that is capable of generating the current density is defined. For example, the current density may require the local shim coil 110 to have a relatively high current density in certain areas and a relatively low current density in other areas. As such, the wiring configuration of the local shim coil 110 may have a relatively high number of loops in the areas in which the high current density is required and a relatively low number of loops in the areas in which the low current density is required. The determined current density is then discretized via a stream function to generate a current density plot (see, e.g., FIG. 3 hereinafter) for the local shim coil 110 having the wiring configuration.

Accordingly, because the local shim coil 110 is configured to reduce the localized magnetic field inhomogeneity, the local shim coil 110 generates a local shimming magnetic field that is counter to (e.g., equal in magnitude and opposite in phase) the localized magnetic field inhomogeneity. As such, the local shim coil 110 effectively reduces the localized magnetic field inhomogeneity caused by the susceptibility artifact 114. Therefore, the local shim coil 110 may improve patient comfort during imaging (e.g., some injured patients experience less pain when their knee is bent during the MRI scan) and/or the local shim coil 110 may improve image quality (e.g., by eliminating (or reducing) the negative effects that the localized magnetic field inhomogeneity has on image quality).

In some embodiments, generating the local shimming magnetic field is referred to as local shimming. In further embodiments, the local shim coil 110 may be the only coil utilized to generate the local shimming magnetic field. In yet further embodiments, the local shim coil 110 may be or may comprise only a single coil (e.g., not a combination of multiple coils). In some embodiments, because the local shim coil 110 may be or may comprise only a single coil, the local shim coil 110 may further reduce the localized magnetic field inhomogeneity caused by the susceptibility artifact 114 (e.g., better mimic the localized magnetic field inhomogeneity). In some embodiments, the above trigonometric series and Equation 1 are collectively referred to as a set of local shim coil configuration equations.

While the perspective views 100*a*-100*c* of FIGS. 1A-1C illustrate the MRI knee coil 101, it will be appreciated that other types of coils are amenable (e.g., elbow coil, wrist coil, etc.). In some embodiments, the other type of coil comprises a local shim coil that is configured to (e.g., via the set of local shim coil configuration equations) to reduce a different localized magnetic field inhomogeneity caused by some other susceptibility artifacts (e.g., some other susceptibility artifact found in the body that causes a localized magnetic field inhomogeneity).

While the perspective views 100*a*-100*c* of FIGS. 1A-1C illustrate the local shim coil 110 bound to the semi-cylindrical surface 112, it will be appreciated that the local shim coil 110 is not limited to being bound on the semi-cylindrical surface 112. Rather, the semi-cylindrical surface 112 may be bound to other specific surfaces, for example, an elliptical surface, a parabolic surface, or the like. It will also be appreciated that the local shim coil 110 may be split into multiple surfaces (e.g., multiple semi-cylindrical surfaces or multiple surfaces having different geometries). It will also be appreciated that the local shim coil 110, instead of being bound (e.g., defined) on a specific surface, may have a three dimensional shape (e.g., a standalone coil) that is placed at a specific location in relation to the susceptibility artifact 114. It will be appreciated that the above equations may then be altered (as needed) to compensate for the chosen geometry of the local shim coil 110 (e.g., on a parabolic surface, on multiple layers, having a three dimensional shape, etc.).

Figure 2:
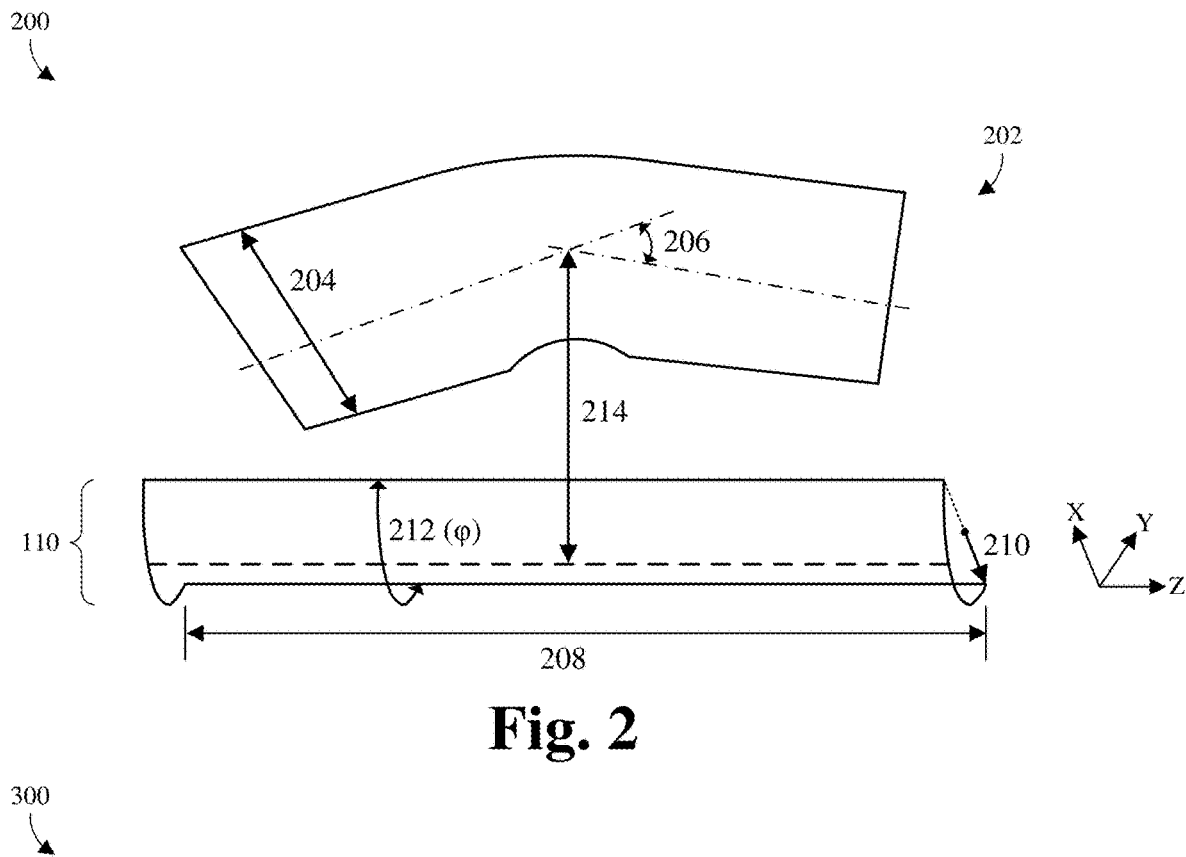
FIG. 2 illustrates a simplified view of some embodiments of the MRI knee coil of FIGS. 1A-1C with a model disposed over the MRI knee coil.

FIG. 2 illustrates a simplified view 200 of some embodiments of the MRI knee coil 101 of FIGS. 1A-1C with a model 202 disposed over the MRI knee coil 101. FIG. 2 is "simplified" because FIG. 2 illustrates merely an outline of the local shim coil 110 (e.g., without any actual wirings).

As shown in the simplified view 200 of FIG. 2, the model 202 is configured to mimic the anatomy of a patient's bent knee. The model 202 comprises a bent knee-like phantom model in which a one (1) parts per million (ppm) tissue susceptibility is disposed within. The bent knee-like phantom has a diameter 204 (e.g., about ten (10) centimeters (cm)) and is bent at an angle 206 (e.g., an angle of about 30 degrees of flexion). An additional air bubble indentation was placed beneath (under) the bent knee-like phantom model. In addition, four (4) millimeters (mm) of a smoothing material (not shown) is disposed between the air bubble indentation and the phantom model to smooth out the permeability transition to achieve a more realistic model of a bent knee. It will be appreciated that the model 202, is merely one example, and other models that mimic the anatomy of a patient's bent knee may be utilized.

Also shown in the simplified view 200 of FIG. 2, the local shim coil 110 has been bound to the semi-cylindrical surface 112. Further, the local shim coil 110 has a length 208 (along the z-axis). In some embodiments, the length 208 is about 25 cm. It will be appreciated that other lengths are amenable. The local shim coil 110 has a radius 210. In some embodiments, the radius 210 is about eight (8) cm. It will be appreciated that other radii are amenable. The local shim coil 110 has a central angle 212. In some embodiments, the central angle 212 is about ninety (90) degrees (e.g., $\pi/2$ in arc radian). It will be appreciated that other central angles are amenable.

Moreover, the local shim coil 110 is disposed a distance 214 below the iso-center of the model 202. In some embodiments, the distance 214 is about eight (8) cm. This geometry of the local shim coil 110 has been chosen, at least partially, due to the shape of some typical MRI knee coil housings (e.g., size, shape, etc.), as well as other design constraints (e.g., patient comfort, MR image resolution, etc.). However, it will be appreciated that, in other embodiments, the geometry (e.g., length, width, radius, arc radian, etc.) of the local shim coil 110 may be different than the local shim coil 110 illustrated in the simplified view 200 of FIG. 2, so that such a local shim coil 110 is specialized for some other MRI coil housing (e.g., a different MRI knee coil housing, an MRI elbow housing, an MRI wrist housing, etc.) and some other localized magnetic field inhomogeneity caused by a particular susceptibility artifact (e.g., some other susceptibility artifact found in the body that causes a localized magnetic field inhomogeneity). As such, it will be appreciated that other lengths, other widths, other radii, other arc radians, and other distances from the iso-center of the model 202 are amenable.

Figure 3:
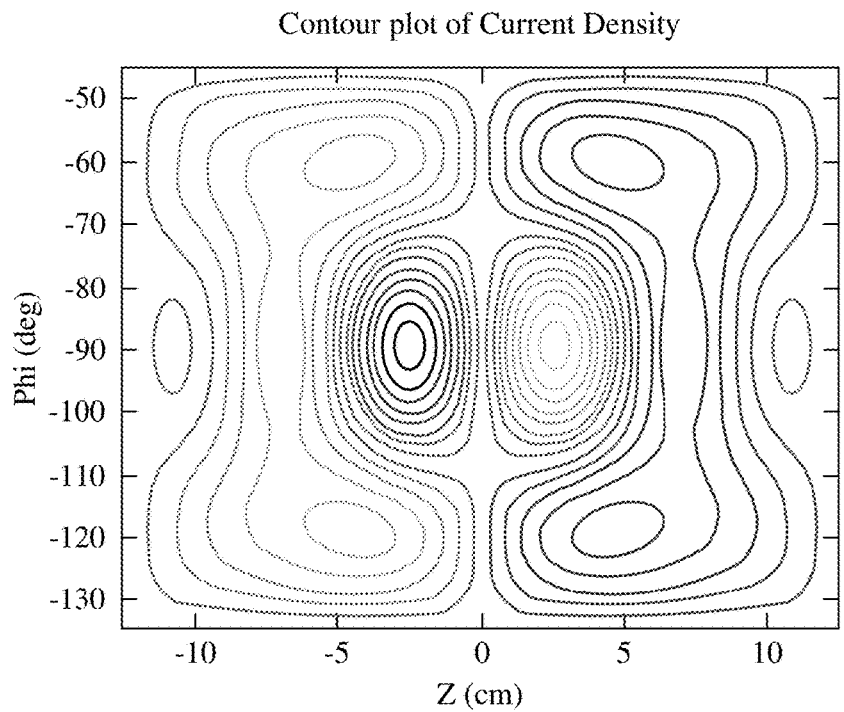
FIG. 3 illustrates a contour plot of a current pattern obtained from a stream function of some embodiments of the local shim coil of the MRI knee coil of FIG. 2.

FIG. 3 illustrates a contour plot 300 of a current pattern obtained from a stream function of some embodiments of the local shim coil 110 of the MRI knee coil 101 of FIG. 2.

Once the geometry of the local shim coil 110 and the target points (e.g., points that correspond to the boundary of the localized magnetic field inhomogeneity) are defined, the current density is calculated based on the above equations. In some embodiments, less than ten (10) target points are chosen. In further embodiments, less than five (5) target points are chosen. In yet further embodiments, two (2) target points are chosen. The number of targets points is chosen so that the boundary of the localized magnetic field is adequately defined without creating an unstable matrix.

The current density is discretized (e.g., via a stream function) and illustrated in the contour plot 300 of FIG. 3. The contour plot 300 illustrates the current density correlating with the positions and current strength of one possible wiring configuration of the local shim coil 110. In some embodiments, the minimum to maximum current density range may be from about 0.0001 milliamps (mAmps) to about five (5) Amps. In some embodiments, the minimum to maximum current density range is about 500 mAmps, while in other embodiments the minimum to maximum current density range may be several Amps (e.g., 2 Amps) depending on the size of the conductor and the size of the $B_0$ inhomogeneity. However, it will be appreciated that other maximum current densities are amenable (e.g., based on the number of windings, gauge of wire, etc.).

Figure 4A:
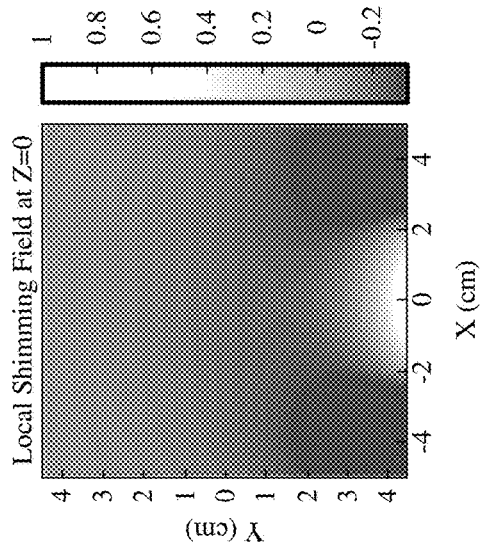
FIGS. 4A-4C illustrate various color scale (grayscale) maps of some embodiments of magnetic fields at the MRI knee coil of FIG. 2 to illustrate the local shim coil reducing a localized magnetic field inhomogeneity caused by a susceptibility artifact.
Figure 4B:
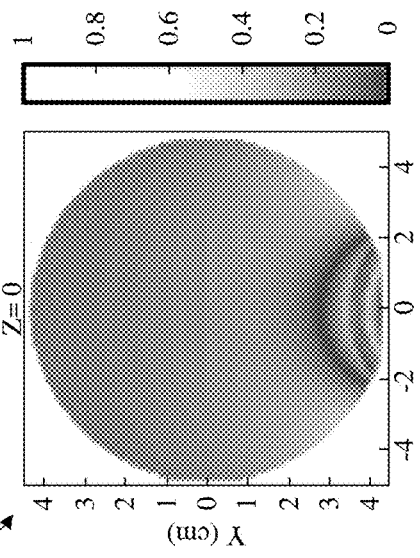
Figure 4C:
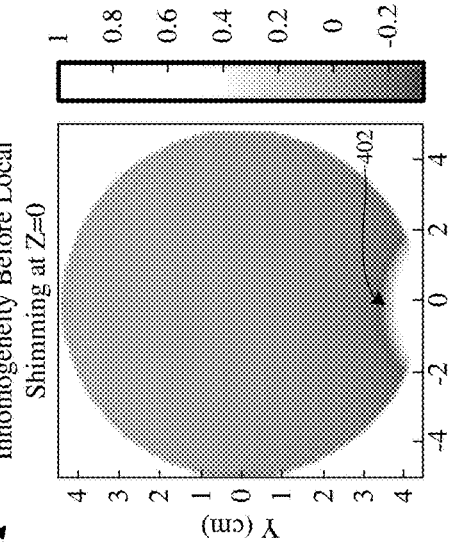

FIGS. 4A-4C illustrate various color scale (grayscale) maps of some embodiments of magnetic fields at the MRI knee coil of FIG. 2 to illustrate the local shim coil 110 reducing a localized magnetic field inhomogeneity 402 caused by a susceptibility artifact 114.

FIG. 4A illustrates a field map 400a of a $B_0$ magnetic field in the Z=0 transverse plane of some embodiments of the model 202 before local shimming.

The model 202 effectively mimics the susceptibility artifact 114 found in a patient's bent knee 108. As such, the model 202 is utilized to simulate and evaluate the $B_0$ shimming performance of the local shim coil 110. As shown in the field map 400a of FIG. 4A, the $B_0$ magnetic field in the Z=0 transverse plane has a magnetic field inhomogeneity 402 before local shimming. The magnetic field inhomogeneity 402 is a deviation of the $B_0$ magnetic field from an average value of the magnetic field.

FIG. 4B illustrates a field map 400b of a local ($B_0$) shimming magnetic field in the Z=0 transverse plane generated by the local shim coil 110.

As shown in the field map 400b of FIG. 4b, the local ($B_0$) shimming magnetic field, which is output by the local shim coil 110, is counter to (e.g., equal in magnitude and opposite in phase) the magnetic field inhomogeneity 402. Further, the local shimming magnetic field effectively mimics the magnetic field inhomogeneity 402 (e.g., the shape and size of the portion of the local shimming magnetic field that counters the magnetic field inhomogeneity 402 is substantially the same as the actual shape and size of the magnetic field inhomogeneity 402).

FIG. 4C illustrates a field map 400c of a $B_0$ magnetic field in the Z=0 transverse plane of some embodiments of the model 202 after the $B_0$ magnetic field has been shimmed by the local shimming magnetic field.

As shown in the field map 400c of FIG. 4c, the local shimming magnetic field effectively reduces the magnetic field inhomogeneity 402. Further, because the local shimming magnetic field effectively mimics the magnetic field inhomogeneity 402, the local shimming magnetic field does not compromise the homogeneity of the rest of the magnetic field. In some embodiments, the local shimming magnetic field reduces the magnetic field inhomogeneity 402 by at least sixty percent (60%). More specifically, the local shimming magnetic field reduces the magnetic field inhomogeneity 402 from 0.15 ppm to 0.06 ppm. In some embodiments, the reduction in the magnetic field inhomogeneity 402 is determined by taking a standard deviation of a lower half of the field map 400c (the upper half is not included in the standard deviation because it is very homogeneous both before and after shimming).

Figure 5A:
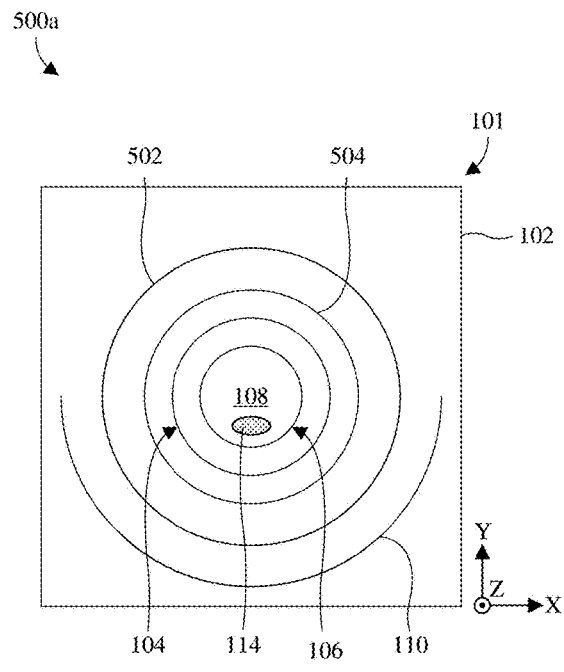
FIGS. 5A-5C illustrate schematic views of some embodiments of the MRI knee coil of FIGS. 1A-1C
Figure 5B:
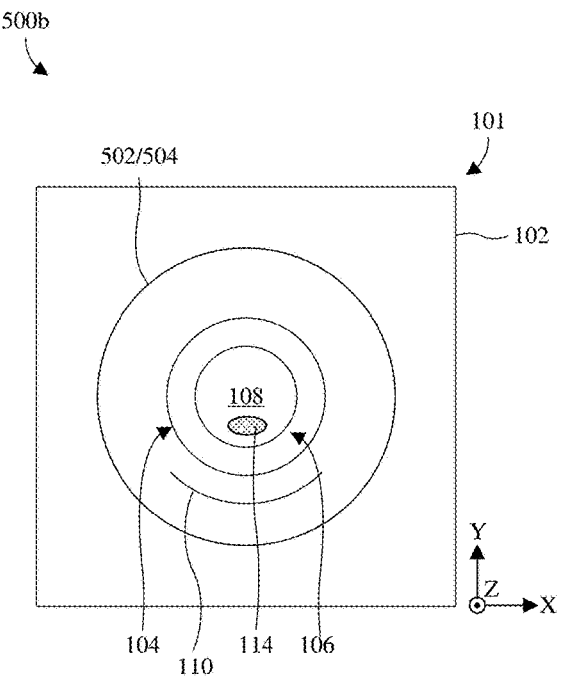
Figure 5C:
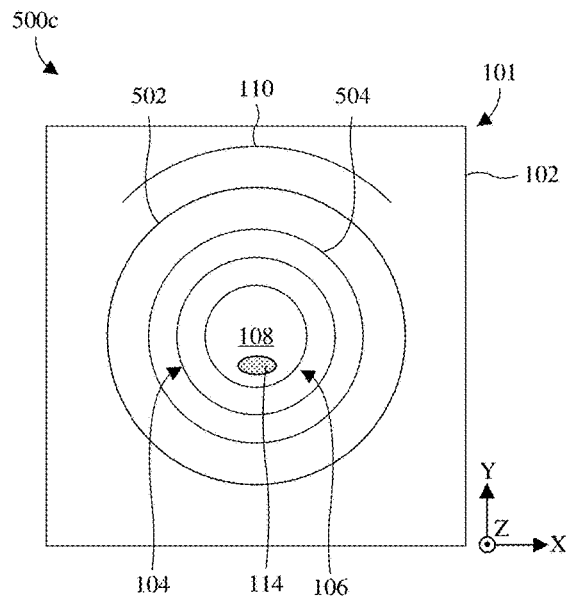

FIGS. 5A-5C illustrate schematic views 500a-500c of some embodiments of the MRI knee coil 101 of FIGS. 1A-1C.

As shown in the schematic views 500a-500c of FIGS. 5A-5C, the MRI knee coil 101 comprises a transmit coil 502, a receive coil 504, and the local shim coil 110. In some embodiments, the transmit coil 502 is referred to as a first electromagnetic coil and the receive coil 504 is referred to as a second electromagnetic coil. The transmit coil 502, the receive coil 504, and the local shim coil 110 are disposed within the housing 102. While not shown in the schematic views 500a-500c of FIGS. 5A-5C, it will be appreciated that the transmit coil 502, the receive coil 504, and the local shim coil 110 each extend laterally along the z-axis (in and out of the page), such that the transmit coil 502, the receive coil 504, and the local shim coil 110 extend laterally between the first side 102a of the housing 102 and the second side 102b of the housing 102.

The transmit coil 502 is configured to output a $B_1$ magnetic field during MRI (e.g., radiofrequency (RF) pulses at the Larmor frequency). The $B_1$ magnetic field excites protons in the patient 106, which causes the excited protons to emit MRI signals. The transmit coil 502 may be or comprise, for example, a birdcage coil, a saddle coil, quadrature coils, parallel transmit coils, some other type of coil suitable as a MRI transmit coil, or a combination of the foregoing. The receive coil 504 is configured to detect MRI signals in response to the excitation of the protons by the transmit coil 502. The receive coil 504 may be or comprise, for example, a birdcage coil, a saddle coil, quadrature coils, phased array coils, some other type of coil suitable as a MRI receive coil, or a combination of the foregoing.

As shown in the schematic view 500a of FIG. 5A, the receive coil 504 extends (wraps) fully around the opening 104 (e.g., central angle of 360 degrees (or 2π radians) around the opening 104). The transmit coil 502 is spaced from the receive coil 504 and extends (wraps) fully around the opening 104 and the receive coil 504 (e.g., central angle of 360 degrees (or 2π radians) around the opening 106). The local shim coil 110 is spaced from both the transmit coil 502 and the receive coil 504. In some embodiments, both the transmit coil 502 and the receive coil 504 are disposed between the opening 104 and the local shim coil 110. In further embodiments, having the both the transmit coil 502 and the receive coil 504 disposed between the opening 104 and the local shim coil 110, proton excitation and detection may be improved. In yet further embodiments, the central angle of the local shim coil 110 (e.g., 180 degrees) is less than a central angle of the transmit coil (e.g., 360 degrees) and/or the receive coil (e.g., 360 degrees).

The local shim coil 110 wraps (e.g., arcs) around the opening 104. In some embodiments, the local shim coil 110 also wraps around the transmit coil 502 and/or the receive coil 504, as illustrate in the schematic view 500a of FIG. 5A. The local shim coil 110 wraps around the opening 104 a first angular amount (e.g., wraps about 180 degrees around the opening 104), and the transmit coil 502 (and/or the receive coil 504) wraps around the opening 106 a second angular amount (e.g., wraps 360 degrees around the opening 104) that is greater than the first angular amount. In other words, the local shim coil 110 arcs circumferentially around a central axis (see, e.g., central axis 113) in a direction from a first radial angle to a second radial angle, and the transmit coil 502 (and/or the receive coil 504) arcs circumferentially around the central axis in the direction from a third radial angle to a fourth radial angle, where a separation in the direction between the third radial angle and the fourth radial angle (e.g., the first angular amount) is greater than a separation in the direction between the first radial angle and the second radial angle (e.g., the second angular amount).

In some embodiments, the local shim coil 110 is disposed beneath (along the y-axis) the opening 104. In some embodiments, because the local shim coil 110 is disposed beneath the opening 104, the local shim coil 110 better mimics and counters the magnetic field inhomogeneity 402 (e.g., due to its closer proximity to the susceptibility artifact 114 in the patient's knee 108). The local shim coil 110 arcs at least partially around the opening 104. For example, as shown in the schematic view 500a of FIG. 5A, in some embodiments, the local shim coil 110 wraps around about half (e.g., 180 degrees (or π radians)) of the opening 104. In some embodiments, because the local shim coil 110 arcs partially around the opening 104, the local shim coil 110 better mimics and counters the magnetic field inhomogeneity 402.

As shown in the schematic view 500b of FIG. 5B, in some embodiments, the transmit coil 502 and the receive coil 504 are a same coil. In such embodiments, a single coil is used to output the $B_1$ magnetic field during MRI and to detect MRI signals in response to the excitation of the protons by the $B_1$ magnetic field. This configuration is different than the configuration illustrated in the schematic view 500a of FIG. 5A. In the schematic view 500a of FIG. 5a, the transmit coil 502 and the receive coil 504 are separated from one another and distinct from one another. In such embodiments, the transmit coil 502 may be a transmit-only coil, which is configured to only output the $B_1$ magnetic field during MRI, and the receive coil 504 is a receive-only coil, which is configured to only detect the MRI signals in response to the excitation of the protons by the $B_1$ magnetic field. Both of these configurations have advantages and disadvantages that are based on the specific requirements of the MRI knee coil 101 (e.g., packaging constraints, image quality, power savings, cost, etc.). It will be appreciated that other configurations are amenable (e.g., comprising a receive-only coil). In other words, the MRI knee coil 101 may comprise the local shim coil 110 with a transmit/receive coil (e.g., one coil that operates in both transmit and receive mode), a receive-only coil (e.g., only one coil that operates in receive mode), or a transmit coil and a receive coil that are separate and distinct from one another.

Also shown in the schematic view 500b of FIG. 5B, the local shim coil 110 is disposed between the opening 104 and the transmit coil 502 and the receive coil 504. In some embodiments, having the local shim coil 110 disposed nearer the opening than the transmit coil 502 and/or the receive coil 504, the local shim coil 110 may be better situated to mimic and counter the magnetic field inhomogeneity 402 (e.g., due to its closer proximity to the susceptibility artifact 114 in the patient's knee 108). Also shown in the schematic view 500b of FIG. 5B, the local shim coil 110 wraps around about a quarter (e.g., 90 degrees (or π/2 radians)) of the opening 104. It will be appreciated that the local shim coil 110 may partially wrap around the opening 106 by other amounts.

As shown in the schematic view 500c of FIG. 5C, in some embodiments, the local shim coil 110 is disposed over (along the y-axis) the transmit coil 502 and the receive coil 504. It will be appreciated that the local shim coil 110 may be situated at other points in the housing 102 in reference to the transmit coil 502 and the receive coil 504. For example, the local shim coil 110 may be disposed on the right (or left) side of both the transmit coil 502 and the receive coil 504. The location of the local shim coil 110 is dependent on design constraints (e.g., receive/transmit power requirements, image quality, patient comfort, etc.) and the location of the susceptibility artifact 114 in the patient 106.

Figure 6:
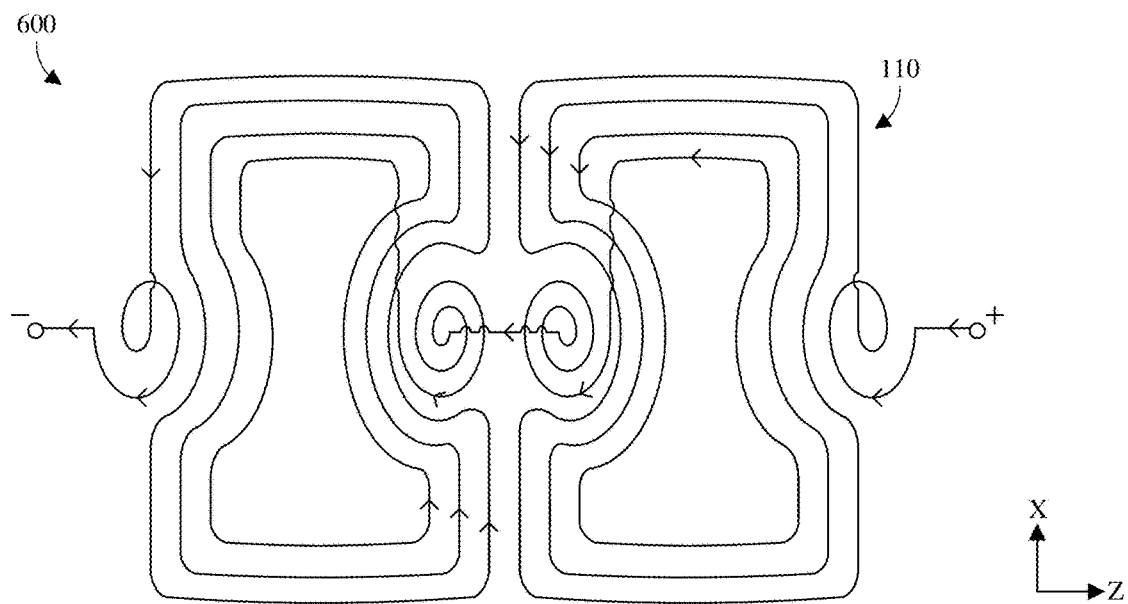
FIG. 6 illustrates a schematic view of some embodiments of the local shim coil of the MRI knee coil of FIGS. 1A-1C.

FIG. 6 illustrates a schematic view 600 of some embodiments of the local shim coil 110 of the MRI knee coil 101 of FIGS. 1A-1C. It will be appreciated that the local shim coil 110 is arced (e.g., π radians, π/2 radians, etc.) but is flattened in FIG. 6 for ease of illustration.

As shown in the schematic view 600 of FIG. 6, the local shim coil 110 has a first wiring configuration. The first wiring configuration is defined by the geometry of the one or more conductors of the local shim coil 110 (e.g., copper wire, coaxial cable, copper sheets, silver wire, conductive traces on a flexible printed circuit board (PCB), etc.). The first wiring configuration is dependent, at least partially, on a current density calculated by the local shim coil configuration equations. For example, as shown in the schematic view 600 of FIG. 6, the local shim coil 110 has a greater number of loops in some areas than in other areas. This configuration is such that the local shim coil 110 is able to generate the determined current density.

The local shim coil 110 is configured to receive direct current (DC) (e.g., illustrated by the positive (+) and negative (−) terminals coupled to opposite ends of the local shim coil 110). As the DC current passes through (e.g., arrows depict DC current flow direction) the one or more conductors of the local shim coil 110, a magnetic field is generated. In some embodiments, a density of the one or more conductors (e.g., more loops for a given area) is different in different areas of the local shim coil 110. The strength of the local shimming magnetic field is stronger in areas in which density of the one or more conductors is greater. Thus, because the local shim coil 110 has the first wiring configuration, the local shim coil 110 generates a local shimming magnetic field that reduces the localized magnetic field inhomogeneity caused by the susceptibility artifact 114. In other words, the first wiring configuration and the DC current are such that the local shim coil 110 generates the local shimming magnetic field. In some embodiments, if alternating current (AC) is passed through the one or more conductors of the local shim coil 110, the local shim coil may not generate a suitable local shimming magnetic field that reduces the localized magnetic field inhomogeneity.

As illustrated in the schematic view 600 of FIG. 6, the first wiring configuration is not a simple wire loop (e.g., 2D loop). Rather, the first wiring configuration is such that the local shim coil 110 outputs the local magnetic shimming coil for at a specific current density. Further, as discussed above, the local shim coil 110 is disposed on a semi-cylindrical surface. Because the local shim coil has the first wiring configuration and is disposed on the semi-cylindrical surface, the local shim coil 110 outputs the local shimming magnetic field when a specific current is passed through the local shim coil 110.

Figure 7:
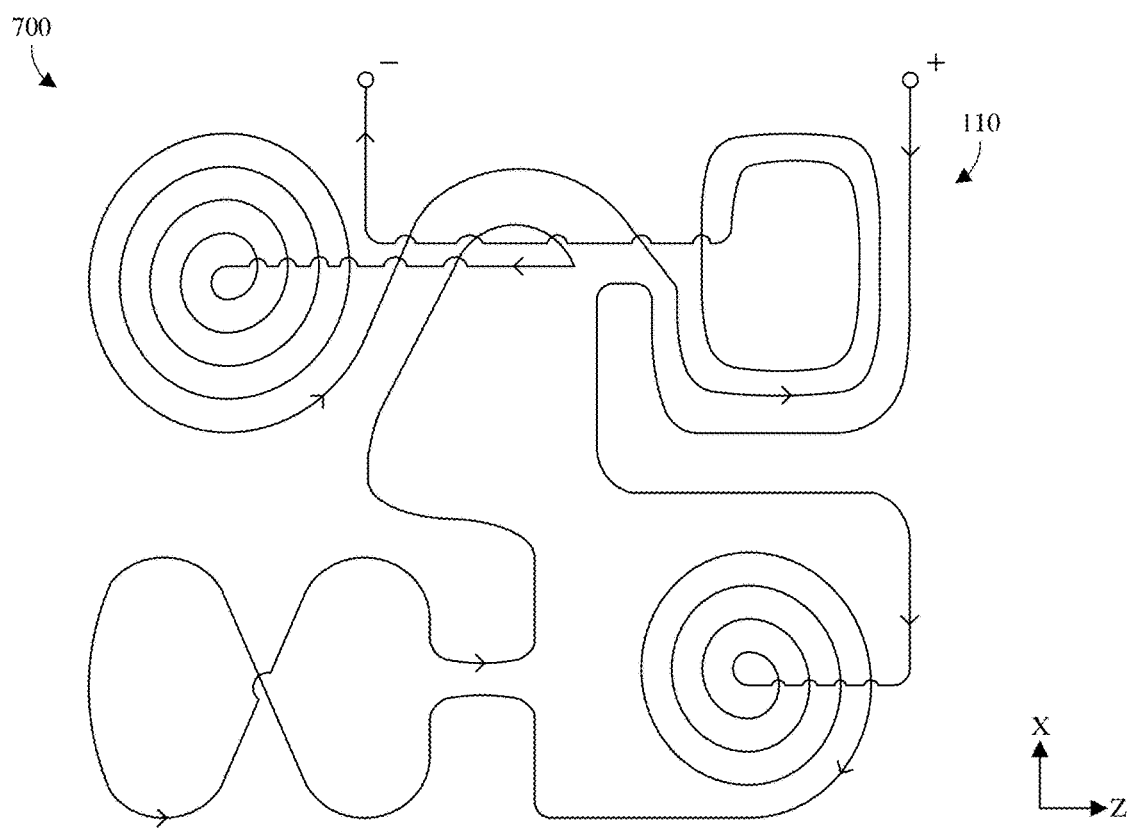
FIG. 7 illustrates a schematic view of some alternative embodiments of the local shim coil of FIG. 6.

FIG. 7 illustrates a schematic view 700 of some alternative embodiments of the local shim coil 110 of FIG. 6.

As shown in the schematic view 700 of FIG. 7, the local shim coil 110 has a second wiring configuration different than the first wiring configuration. In some embodiments, the local shim coil 110 having the second wiring configuration is configured to generate a local shimming magnetic field (e.g., first local shimming magnetic field) that is different than the local shimming magnetic field generated by the local shim coil 110 having the first wiring configuration (e.g., second local shimming magnetic field).

In some embodiments, the first local shimming magnetic field and the second local shimming magnetic field are configured to reduce a same localized magnetic field inhomogeneity. In other embodiments, the first local shimming magnetic field and the second local shimming magnetic field are configured to reduce a different localized magnetic field inhomogeneity. For example, the first local shimming magnetic field may be configured to reduce the localized magnetic field inhomogeneity caused by the susceptibility artifact found in a patient's bent knee, whereas the second local shimming magnetic field may be configured to reduce the localized magnetic field inhomogeneity caused by a susceptibility artifact found in a different part of the body (e.g., the elbow, the wrist, etc.). In further embodiments, the local shim coil 110 having the second wiring configuration may be disposed in a different housing (and thus have different geometries, such as different lengths, different widths, different radii, different arc radians, and/or different distances from the iso-center of a susceptibility artifact) and/or be configured to receive a different strength of DC current than the local shim coil 110 having the first wiring configuration.

Figure 8:
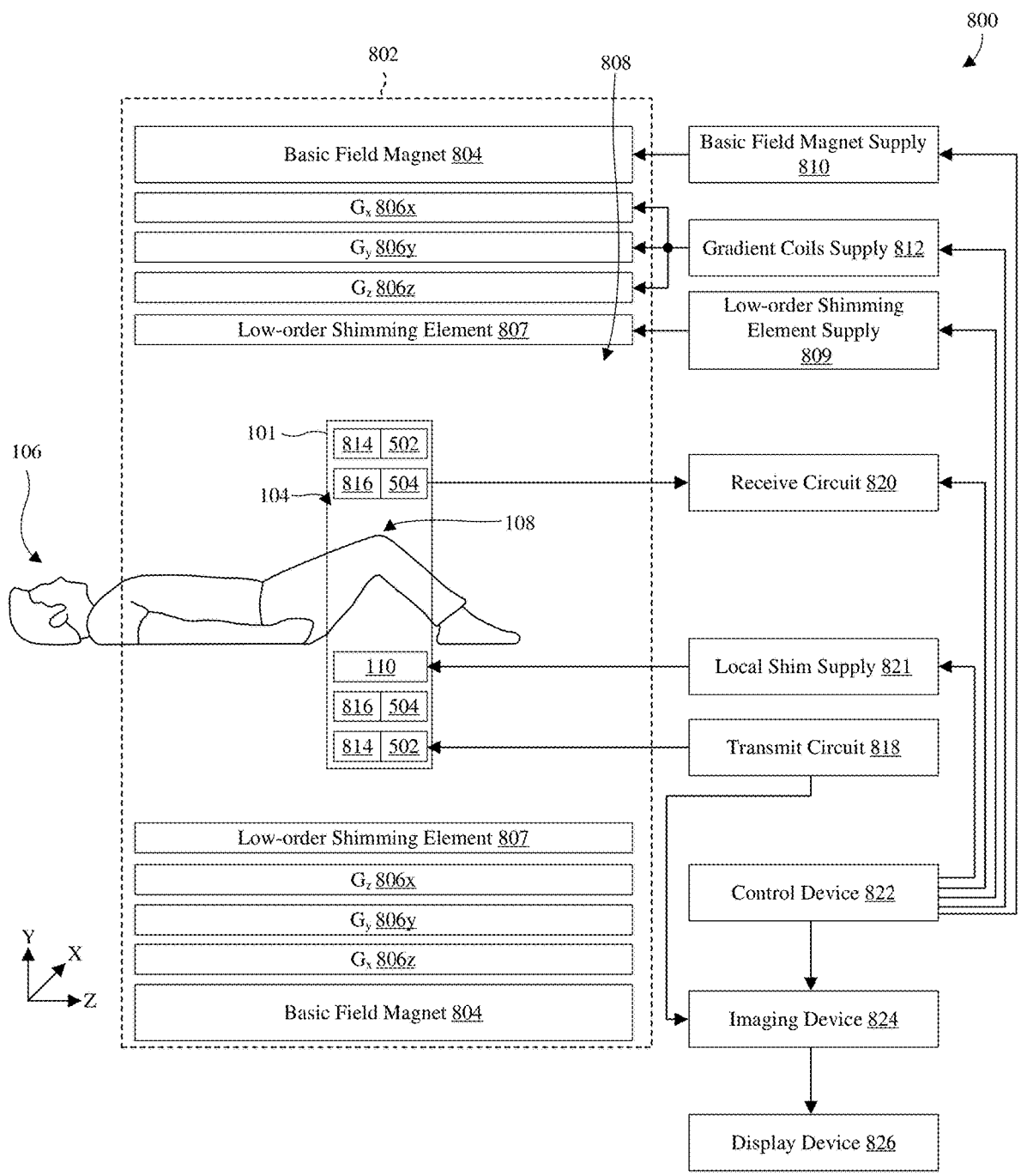
FIG. 8 illustrates a block diagram of some embodiments of an MRI system comprising an MRI knee coil in which a local shim coil reduces a localized magnetic field inhomogeneity.

FIG. 8 illustrates a block diagram 800 of some embodiments of an MRI system comprising an MRI knee coil 101 in which a local shim coil 110 reduces a localized magnetic field inhomogeneity. The MRI knee coil 101 may, for example, be as in any one or combination of FIGS. 1A-1C, 2, 3, 4A-4C, 5A-5C, 6, and 7.

The MRI system comprises a scanner 802 in which a basic field magnet 804, a plurality of gradient coils 806x-806z, and a low-order shimming element 807 are arranged. The basic field magnet 804, the gradient coils 806x-806z, and the low-order shimming element 807 are arranged around a bore 808 of the scanner 802, which receives a patient 106 and the MRI knee coil 101 while arranged on the patient 106 (e.g., the patient's knee 108 is positioned within the opening 104 of the MRI knee coil 101). The basic field magnet 804 is electrically coupled to, and controlled in part by, a basic field magnet power supply 810. The basic field magnet 804 produces a $B_0$ magnetic field over the patient 106 (e.g., within the bore 808). In some embodiments, the $B_0$ magnetic field strength is 7 tesla (T) or above, but other suitable $B_0$ magnetic field strengths are amenable (e.g., 1.5 T, 3.0 T, etc.).

The plurality of gradient coils 806x-806z emit gradient magnetic fields to spatially encode MRI signals received from the patient 106. The plurality of gradient coils 806x-806z include an x-direction gradient coil 806x, a y-direction gradient coil 806y, and a z-direction gradient coil 806z for spatially encoding the MRI signals respectively in the X direction, the Y direction, and the Z direction. The Z direction is parallel to the $B_0$ magnetic field produced by the basic field magnet 804, whereas the X and Y directions are transverse to the $B_0$ magnetic field. In alternative embodiments, one or more of the gradient coils 806x-806z is/are omitted. The gradient coils 806x-806z are electrically coupled to, and controlled in part, by a gradient coil power supply 812.

The low-order shimming element 807 is configured to reduce unwanted globalized spherical harmonic components. The low-order shimming element is capable of correcting spatially globalized magnetic field distortions, but is unable to adequately correct localized magnetic field distortions. In further embodiments, the low-order shimming element 807 may be a passive low-order shimming element (e.g., affixed ferromagnetic structures) and/or an active low-order shimming element (e.g., a discrete shimming coil and/or one or more of the gradient coils 806z-806z can be utilized as active low-order shimming elements). The low-order shimming element 807 is electrically coupled to, and controlled in part, by a low-order shimming element power supply 809.

In some embodiments, the scanner 802 is devoid of a built-in transmit coil. In such embodiments, the MRI depends upon the transmit coil 502 of the MRI knee coil 101. For example, the scanner 802 may be devoid of a primary coil and/or a whole body coil (WBC). In other embodiments, the scanner 802 has a primary coil and/or a WBC suitable for use as a built-in transmit coil. In such alternative embodiments, either the transmit coil 502 of the MRI knee coil 101 or the built-in transmit coil of the scanner 802 may be used for MRI. However, because the MRI knee coil 101 is local and would hence be closer to the patient 106 than the built-in transmit coil, the MRI knee coil 101 may be preferred.

The MRI knee coil 101 comprises the transmit coil 502, a receive coil 504, and a local shim coil 110. The MRI knee coil 101 (and the patient 106) are able to be moved in and out of the bore 808 (along the z-axis) of the scanner 802 (e.g., via a slide table that moves in and out of the bore 808). The transmit coil 502 comprise or is otherwise associated with a transmit control circuit 814. The transmit control circuit 814 disables the transmit coil 502 when the MRI system operates in receive mode. The receive coil 504 comprises or is otherwise associated with a decoupling circuit 816. The decoupling circuit 816 decouples the receive coil 504 from the $B_1$ magnetic field when the MRI system operates in transmit mode. In some embodiments, the decoupling circuit 816 comprises a decoupling unit for each individual loop and/or element of the receive coil 504. It will be appreciated that, in some embodiments, a single coil is configured to operate in both transmit and receive mode. In such embodiments, the single coil comprises or is otherwise associated with both the transmit control circuit 814 and the decoupling circuit 816.

A transmit circuit 818 and a receive circuit 820 are electrically coupled to the MRI knee coil 101. The transmit circuit 818 is electrically coupled to and drives the transmit coil 502 to generate a $B_1$ magnetic field transverse to the $B_0$ magnetic field when the MRI system operates in transmit mode. For example, the transmit circuit 818 may drive the transmit coil 502 to generate radiofrequency (RF) pulses at the Larmor frequency. The transmit circuit 818 is configured to provide an alternating current (AC) to the transmit coil 502 so that the transmit coil 502 generates the $B_1$ magnetic field (e.g., the transmit coil 502 outputs the $B_1$ field in response to receiving the AC current). It will be appreciated that, in some embodiments, the transmit circuit 818 provides signals to a transmit circuit power supply (not shown) that then provides the AC current to the transmit circuit 818. The $B_1$ magnetic field excites protons in the patient 106, which causes to the protons to emit MRI signals. The decoupling circuit 816 decouples the receive coil 504 from the $B_1$ magnetic field during transmit mode. The receive circuit 816 is electrically coupled to the receive coil 504 and receives the MRI signals in response to excitation of the protons by the transmit coil 502. As describe above, the transmit control circuit 814 disables the transmit coil 502 during receive mode.

In some embodiments, the transmit circuit 818 and/or the receive circuit 820 are disposed in the scanner 802 (e.g., in a housing of the scanner 802). In other embodiments, the transmit circuit 818 and/or the receive circuit 820 are disposed in the MRI knee coil 101 (e.g., in the housing 102 of the MRI knee coil 101). In other embodiments, the transmit circuit 818 and/or the receive circuit 820 are disposed outside the MRI knee coil 101 and the scanner 802.

The local shim coil 110 is electrically coupled to a local shim power supply 821. The local shim power supply 821 is configured to provide DC current so that the local shim coil 110 generates a local shimming magnetic field within the opening 104 of the MRI knee coil 101. For example, the local shim power supply 821 is configured to selectively provide DC current to the local shim coil 110, such that the local shim coil 110 generates a local shimming magnetic field that reduce a localized magnetic field inhomogeneity caused by a susceptibility artifact 114. In some embodiments, the local shim power supply 821 comprises an AC to DC converter (e.g., a rectifier).

The basic field magnet power supply 810, the gradient coil power supply 812, the low-order shimming element power supply 809, the transmit circuit 818, the local shim power supply 821, or any combination of the foregoing is/are controlled by a control device 822. For example, the control device 822 provides signals to the local shim power supply 821 so that the local shim power supply 821 selectively provides DC current to the local shim coil 110. In some embodiments, the control device 822 is disposed within the scanner 802 (e.g., housing of the scanner 802). In other embodiments, the control device 822 is disposed outside the scanner 802. The transmit coil 502, the receive coil 504, and/or the local shim coil 110 may be inductively coupled (e.g., via a whole body coil in the scanner 802 (not shown)) or directly coupled (e.g., via a physical connection, such as one or more conductive wires) to the scanner 802. In further embodiments, the MRI knee coil 101 maybe coupled to the scanner 802 via, for example, a coaxial cable, a wireless transmitter, or the like.

An imaging device 824 receives MRI signals from the receive circuit 820 and, in some embodiments, receives control signals from the control device 822. Based thereon, the imaging device 824 generates an image of the patient 106 and outputs the image to a display device 826. The imaging device 824 generates the image by performing a transformation process on the MRI signals, such as, for example, a two-dimensional fast Fourier transform (FFT) or some other suitable transform. The control device 822 may, for example, be a general-purpose device (e.g., a computer) executing instructions or an application-specific device. Similarly, the imaging device 824 may, for example, be a general-purpose device (e.g., a computer) executing instructions or an application-specific device. While the control device 822 and the imaging device 824 are shown as being separate, the control device 822 and the imaging device 824 may be integrated together in alternative embodiments.

While the block diagram 800 of FIG. 8 illustrates the MRI knee coil 101, it will be appreciated that other types of MRI coils (e.g., elbow coils, wrist coils, etc.) that comprise a local shim coil that is configured to reduce a different localized magnetic field inhomogeneity caused by some other susceptibility artifacts (e.g., some other susceptibility artifact found in the body that causes a localized magnetic field inhomogeneity) are amenable.

Figure 9:
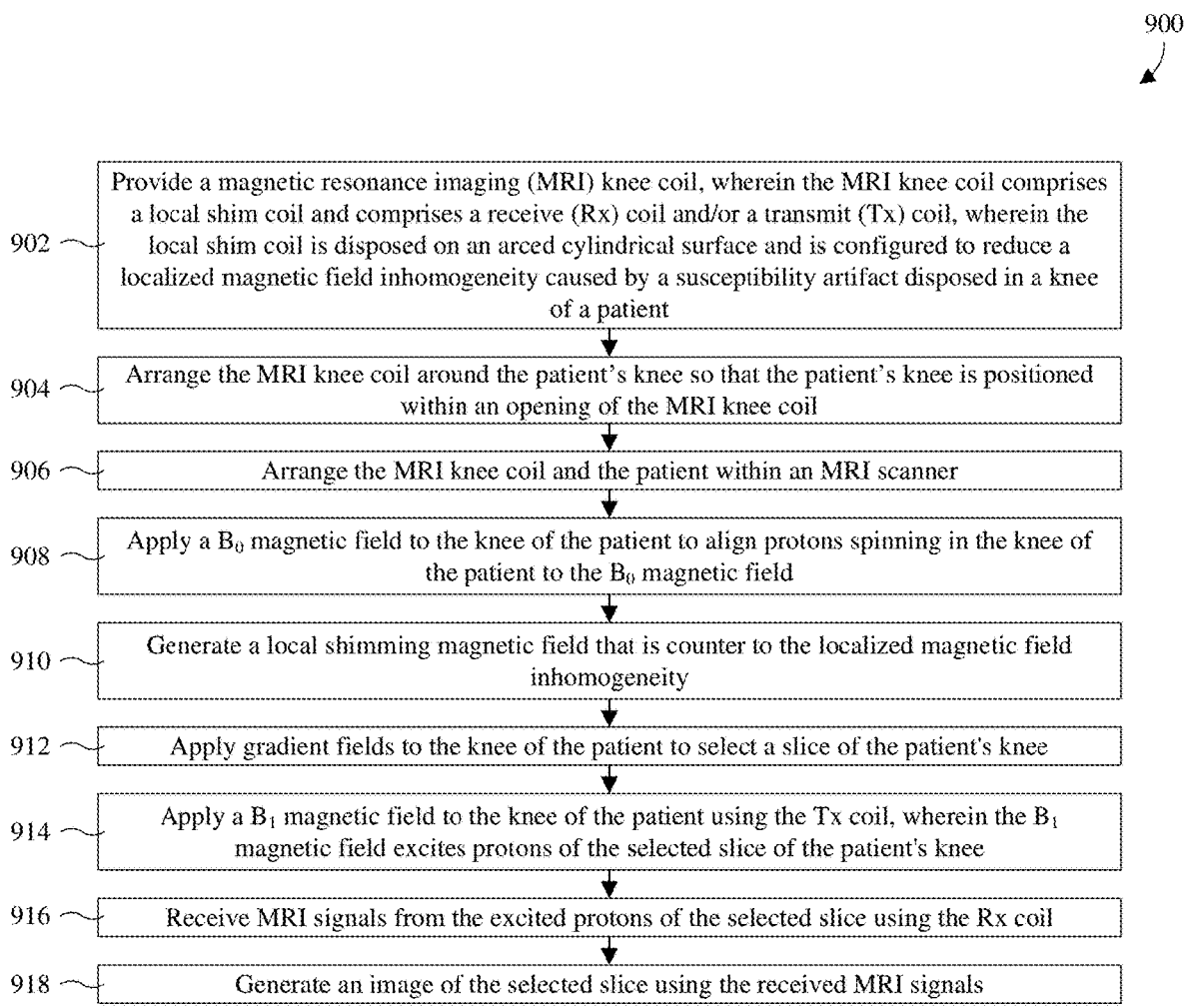
FIG. 9 illustrates a flowchart of some embodiments of a method for performing an MRI process using an MRI knee coil in which a local shim coil reduces a localized magnetic field inhomogeneity.

FIG. 9 illustrates a flowchart 900 of some embodiments of a method for performing an MRI process using an MRI knee coil in which a local shim coil 110 reduces a localized magnetic field inhomogeneity. The MRI knee coil 101 may, for example, be as in any one or combination of FIGS. 1A-1C, 2, 3, 4A-4C, 5A-5C, 6, 7, and 8. Further, the MRI process may, for example, be performed by the MRI system of FIG. 8 or some other suitable MRI system.

While the flowchart 900 of FIG. 9 is illustrated and described herein as a series of acts or events, it will be appreciated that the illustrated ordering of such acts or events is not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

At 902, a MRI knee coil is provided. The MRI knee coil comprises a local shim coil and comprises a receive coil and/or a transmit coil, wherein the local shim coil is disposed on an arced cylindrical surface and is configured to reduce a localized magnetic field inhomogeneity caused by a susceptibility artifact disposed in a knee of a patient. The local shim coil is configured to reduce the localized magnetic field inhomogeneity by, at least partially, the set of local shim coil configuration equations. Because the local shim coil is configured to reduce the localized magnetic field inhomogeneity, the local shim coil generates a local shimming magnetic field that is counter to (e.g., equal in magnitude and opposite in phase) the localized magnetic field inhomogeneity. See, for example, the MRI knee coil 101 of FIGS. 1A-1C, 5A-5C, 6, 7, and 8.

At 904, the MRI knee coil is arranged around the patient's knee so that the patient's knee is positioned within an opening of the MRI knee coil. See, for example, the MRI knee coil 101 and the patient 106 in FIGS. 1A, 1C, 2, 5, and 8.

At 906, the MRI knee coil and the patient are arranged within an MRI scanner. For example, the patient and the MRI knee coil are moved into a bore of the MRI scanner on a slide table. See, for example, the scanner 802 of FIG. 8.

At 908, a $B_0$ magnetic field is applied to the knee of the patient to align protons spinning in the knee to the $B_0$ magnetic field. The $B_0$ magnetic field may, for example, be applied by the basic field magnet 804 of FIG. 8 and the basic field magnet power supply 810 of FIG. 8.

At 910, a local shimming magnetic field that is counter to the localized magnetic field inhomogeneity is generated. The local shimming magnetic field may, for example, be generated by the local shim coil 110 of FIG. 8 and the local shim power supply 821 of FIG. 8. By generating the local shimming magnetic field, the localized magnetic field inhomogeneity caused by the susceptibility artifact is effectively reduced. Therefore, the local shim coil may improve patient comfort during imaging (e.g., some injured patients experience less pain when their knee is bent during the MRI scan) and/or the local shim coil may improve image quality (e.g., by eliminating (or reducing) the negative effects that the localized magnetic field inhomogeneity has on image quality).

At 912, gradient fields are applied to the knee of the patient to select a slice of the patient's knee. The gradient fields may, for example, be applied by the gradient coils 806x-806z of FIG. 8 and the gradient coil power supply 812 of FIG. 8.

At 914, a $B_1$ magnetic field is applied to the knee of the patient using the transmit coil, wherein the $B_1$ magnetic field excites protons of the selected slice of the patient's knee. The $B_1$ magnetic field may, for example, be applied by the transmit coil 502 of FIG. 8 and the transmit circuit 818 of FIG. 8. Further, the receive coil 504 may, for example, be decoupled from the $B_1$ magnetic field by the decoupling circuit 816 of FIG. 8 during transmission of the $B_1$ magnetic field.

At 916, MRI signals are received from the excited protons of the selected slice using the receive coil. The MRI signals may, for example, be received by the receive coil 504 of FIG. 8 and the receive circuit 820 of FIG. 8. Further, the transmit coil 502 may be disabled by the transmit control circuit 814 of FIG. 8 while receiving the MRI signals.

At 918, an image of the selected slice is generated using the received MRI signals. The image may, for example, be generated by the imaging device 824 of FIG. 8 and/or may, for example, be displayed on the display device 826 of FIG. 8.

While the flowchart 900 above is described in reference to an MRI knee coil that reduces the localized magnetic field inhomogeneity caused by the susceptibility artifact disposed in a patient's knee, it will be appreciated that other types of MRI coils (e.g., elbow coils, wrist coils, etc.) that comprise a local shim coil that is configured to reduce a different localized magnetic field inhomogeneity caused by some other susceptibility artifacts (e.g., some other susceptibility artifact found in the body that causes a localized magnetic field inhomogeneity) are amenable.

In view of the foregoing, some embodiments of the present disclosure provide a MRI knee coil including: a housing having an opening, wherein the opening extends laterally between a first side of the housing and a second side of the housing opposite the first side of the housing such that a knee of a patient is positioned within the opening; a first electromagnetic coil disposed in the housing, wherein the first electromagnetic coil is a transmit coil or a receive coil or both; and a local shim coil disposed in the housing and spaced from the first electromagnetic coil, wherein the local shim coil has one or more conductors, wherein each of the one or more conductors of the local shim coil is disposed on a semi-cylindrical surface, wherein the semi-cylindrical surface extends laterally from the first side of the housing to the second side of the housing, and wherein the local shim coil is configured to generate a local shimming magnetic field that reduces a localized magnetic field inhomogeneity caused by a susceptibility artifact disposed in the knee of the patient. In some embodiments, the local shim coil reduces the localized magnetic field inhomogeneity due to a direct current (DC) passing through the one or more conductors. In some embodiments, the first electromagnetic coil is a transmit-only coil that is configure to output a $B_1$ magnetic field in response to receiving an alternating current (AC). In some embodiments, the local shim coil is disposed between the first electromagnetic coil and the opening. In some embodiments, the first electromagnetic coil is disposed between the opening and the local shim coil. In some embodiments, a second electromagnetic coil disposed in the housing, wherein the second electromagnetic coil is spaced from both the first electromagnetic coil and the local shim coil, and wherein the first electromagnetic coil is a transmit-only coil and the second electromagnetic coil is a receive-only coil. In some embodiments, the semi-cylindrical surface wraps only partially around the opening. In further embodiments, the first electromagnetic coil wraps around the opening a first angular amount; and the semi-cylindrical surface wraps around the opening a second angular amount less than the first angular amount. In further embodiments, the first electromagnetic coil wraps fully around the opening, such that the opening extends laterally between the first side of the housing and the second side of the housing within a perimeter of the first electromagnetic coil. In yet further embodiments, a length of the local shim coil is substantially equal to 25 centimeters (cm); a radius of the local shim coil is substantially equal to 8 cm; and the local shim coil has a central angle that is less than or equal to 180 degrees.

In some embodiments, the present disclosure further provides an MRI system including an MRI knee coil, wherein the MRI knee coil includes: a housing having an opening, wherein the opening is configured so that a knee of a patient is positioned in the opening; an electromagnetic coil disposed in the housing, wherein the electromagnetic coil is a transmit coil or a receive coil or both, wherein the electromagnetic coil arcs circumferentially around a central axis in a direction from a first radial angle to a second radial angle, and wherein the central axis extends laterally though the opening; and a local shim coil disposed in the housing and spaced from the electromagnetic coil, wherein the local shim coil arcs circumferentially around the central axis in the direction from a third radial angle to a fourth radial angle, wherein a separation between the first and second radial angles in the direction is greater than a separation between the third and fourth radial angles in the direction, wherein the local shim coil is disposed on a semi-cylindrical surface, wherein the local shim coil generates a local shimming magnetic field that has a same magnitude and an opposite phase as a localized magnetic field inhomogeneity, and wherein the localized magnetic field inhomogeneity is caused by a susceptibility artifact disposed in the patient. In some embodiments, the MRI system further includes an MRI scanner having a basic field magnet disposed around a bore of the MRI scanner, wherein the basic field magnet is configured to generate a B0 magnetic field in the bore, wherein the local shim coil is configured to generate the local shimming magnetic field in the bore of the MRI scanner. In further embodiments, the localized magnetic field inhomogeneity is an inhomogeneity in the B0 magnetic field. In yet further embodiments, the MRI system having a plurality of gradient coils disposed around the bore of the MRI scanner and a low-order shimming element disposed around the bore of the MRI scanner. In some embodiments, the MRI system includes a local shim power supply that is configured to provide a direct current (DC) to the local shim coil so that the local shim coil generates the local shimming magnetic field. In further embodiments, the separation between the third radial angle and the fourth radial angle in the direction is less than or equal to 180 degrees. In yet further embodiments, the electromagnetic coil wraps fully around the opening, such that the opening is disposed within a perimeter of the electromagnetic coil.

In some embodiments, the present disclosure further provides a method for MRI including, providing an MRI knee coil having: a housing having an opening, wherein the opening extends laterally in a first direction through the housing such that a knee of a patient is positioned within the opening; an electromagnetic coil disposed in the housing, wherein the electromagnetic coil is a transmit coil or a receive coil or both; and a local shim coil disposed in the housing and spaced from the electromagnetic coil, wherein the local shim coil has one or more conductors, wherein each of the one or more conductors of the local shim coil is disposed on a semi-cylindrical surface, and wherein the semi-cylindrical surface extends laterally in the first direction; positioning the knee of the patient within the opening, such that the knee of the patient is bent at an angle and disposed between opposite sides of the housing; providing a first current to the local shim coil to generate a local shimming magnetic field that reduces a localized magnetic field inhomogeneity caused by a susceptibility artifact disposed in the knee of the patient; and performing an MRI process on the patient using the MRI knee coil, wherein the MRI process generates an image of the patient. In some embodiments, the method for MRI includes generating a B0 magnetic field during, wherein the localize magnetic field inhomogeneity is an inhomogeneity of the B0 magnetic field and providing a second current to the electromagnetic coil to generate a $B_1$ magnetic field that is transverse the B0 magnetic field. In further embodiments, the first current is a direct current (DC).

The following includes definitions of selected terms employed herein. The definitions include various examples or forms of components that fall within the scope of a term and that may be used for implementation. The examples are not intended to be limiting. Both singular and plural forms of terms may be within the definitions.

The terminology used herein is for the purpose of describing particular embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which embodiments belong. It will be further understood that terms (e.g., those defined in commonly used dictionaries) should be interpreted as having a meaning that is consistent with their meaning in the context of the relevant art and will not be interpreted in an idealized or overly formal sense unless expressly so defined herein.

In the above description, some components may be displayed in multiple figures carrying the same reference signs but may not be described multiple times in detail. A detailed description of a component may then apply to that component for all its occurrences.

The detailed descriptions presented herein may be presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on refer to actions and processes of a computer system, logic, processor, or similar electronic device that manipulates and transforms data represented as physical and/or electronic quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

What is claimed is:

1. A magnetic resonance imaging (MRI) knee coil comprising:

a housing comprising an opening, wherein the opening extends laterally between a first side of the housing and a second side of the housing opposite the first side of the housing such that a knee of a patient is positionable within the opening;

a first electromagnetic coil disposed in the housing, wherein the first electromagnetic coil is a transmit coil or a receive coil or both; and a local shim coil disposed in the housing and spaced from the first electromagnetic coil, wherein the local shim coil comprises one or more conductors, wherein each of the one or more conductors of the local shim coil is localized on a semi-cylindrical surface, wherein the semi-cylindrical surface has a length extending laterally from the first side of the housing to the second side of the housing and further has a radius orthogonal to the length, wherein the local shim coil is configured to generate a local shimming magnetic field that reduces a localized magnetic field inhomogeneity caused by a susceptibility artifact disposed in the knee of the patient, wherein the one or more conductors form a plurality of sets of loops, each having a plurality of concentric loops of varying sizes, and wherein the plurality of sets of loops comprise a first set of loops proximate a center of the length, and further comprise a second set of loops into which the first set of loops is laterally recessed in a first direction away from the center along the length.

2. The MRI knee coil of claim 1, wherein the local shim coil generates the local shimming magnetic field due to a direct current (DC) passing through the one or more conductors.

3. The MRI knee coil of claim 1, further comprising:

a second electromagnetic coil disposed in the housing, wherein the second electromagnetic coil is spaced from both the first electromagnetic coil and the local shim coil, and wherein the first electromagnetic coil is a transmit-only coil and the second electromagnetic coil is a receive-only coil.

4. The MRI knee coil of claim 1, wherein:

the first electromagnetic coil wraps around the opening a first angular amount; and the semi-cylindrical surface wraps around the opening a second angular amount less than the first angular amount.

5. The MRI knee coil of claim 1, wherein the local shim coil is an only local shim coil of the MRI knee coil, and the plurality of sets of loops are formed by a single continuous wire.

6. The MRI knee coil of claim 1, wherein the plurality of sets of loops comprise a third set of loops proximate the center of the length and on an opposite side of the center as the first set of loops along the length, wherein the plurality of sets of loops comprises a fourth set of loops into which the third set of loops is laterally recessed in a second direction away from the center along the length, and wherein the second direction is opposite the first direction.

7. The MRI knee coil of claim 6, wherein the first set of loops mirrors the third set of loops, and wherein the second set of loops mirrors the fourth set of loops.

8. A method for magnetic resonance imaging (MRI) comprising:
providing an MRI knee coil comprising:
a housing comprising an opening, wherein the opening extends laterally in a first direction through the housing such that a knee of a patient is positionable within the opening;
an electromagnetic coil disposed in the housing, wherein the electromagnetic coil is a transmit coil or a receive coil or both;
a local shim coil disposed in the housing and spaced from the electromagnetic coil, wherein the local shim coil comprises one or more conductors, wherein each of the one or more conductors of the local shim coil is localized on a semi-cylindrical surface, and wherein the semi-cylindrical surface extends laterally in the first direction;
positioning the knee of the patient within the opening, such that the knee of the patient is bent at an angle and disposed between opposite sides of the housing;
providing a first current to the local shim coil to generate a local shimming magnetic field that reduces a localized magnetic field inhomogeneity caused by a susceptibility artifact disposed in the knee of the patient; and
performing an MRI process on the patient using the MRI knee coil, wherein the MRI process generates an image of the patient;
wherein the local shim coil is an only local shim coil used to reduce the localized magnetic field inhomogeneity during the MRI process, and wherein the one or more conductors form a plurality of sets of loops laid out so a density of the one or more conductors varies across the semi-cylindrical surface in correlation to a current density plot, which is determined across the semi-cylindrical surface to produce the local shimming magnetic field with a minimum amount of magnetic energy possible.

9. The method of claim 8, further comprising:
generating a $B_0$ magnetic field, wherein the localized magnetic field inhomogeneity is an inhomogeneity of the $B_0$ magnetic field; and
providing a second current to the electromagnetic coil to generate a $B_1$ magnetic field that is transverse to the $B_0$ magnetic field.

10. The method of claim 9, wherein the first current is a direct current (DC).

11. The method of claim 8, wherein the one or more conductors comprises a single conductive wire, and wherein the providing of the MRI knee coil comprises:
determining the current density plot across the semi-cylindrical surface using a target field method; and
winding the single conductive wire on the semi-cylindrical surface to form the plurality of sets of loops so the density of the one or more conductors varies across the semi-cylindrical surface in correlation with the current density plot.

12. The method of claim 8, wherein each set of the plurality of sets of loops has a plurality of concentric loops of varying sizes, wherein the plurality of sets of loops comprises a first set of loops and a second set of loops, and wherein the first set of loops and the second set of loops border each other and are directly under the localized magnetic field inhomogeneity upon positioning of the knee within the opening.

13. The method of claim 12, wherein the plurality of sets of loops comprises a third set of loops and a fourth set of loops respectively on the opposite sides of the housing and between which the first and second sets of loops are arranged, and wherein the first and second sets of loops are laterally and respectively recessed into the third and fourth sets of loops.

14. A magnetic resonance imaging (MRI) system comprising an MRI knee coil, wherein the MRI knee coil comprises:
a housing comprising an opening, wherein the opening extends laterally between a first side of the housing and a second side of the housing opposite the first side of the housing such that a knee of a patient is positionable within the opening;
a first electromagnetic coil disposed in the housing, wherein the first electromagnetic coil is a transmit coil or a receive coil or both; and
a local shim coil disposed in the housing and spaced from the first electromagnetic coil, wherein the local shim coil comprises one or more conductors, wherein each of the one or more conductors of the local shim coil is disposed on a semi-cylindrical surface, wherein the semi-cylindrical surface has a length extending laterally from the first side of the housing to the second side of the housing and further has a radius orthogonal to the length, wherein the local shim coil is configured to generate a local shimming magnetic field that reduces a localized magnetic field inhomogeneity caused by a susceptibility artifact disposed in the knee of the patient, wherein the one or more conductors comprise a continuous conductor forming a plurality of sets of loops, each having a plurality of concentric loops of varying sizes, and wherein the plurality of sets of loops comprise a first set of loops proximate a center of the length, and further comprise a second set of loops into which the first set of loops is laterally recessed in a first direction away from the center along the length.

15. The MRI system according to claim 14, wherein:
the first electromagnetic coil arcs circumferentially around a central axis in a second direction from a first radial angle to a second radial angle;
the central axis extends laterally though the opening;
the local shim coil arcs circumferentially around the central axis in the second direction from a third radial angle to a fourth radial angle; and
a separation between the first and second radial angles in the second direction is greater than a separation between the third and fourth radial angles in the second direction.

16. The MRI system according to claim 14, further comprising:
an MRI scanner comprising a basic field magnet disposed around a bore of the MRI scanner, wherein the basic field magnet is configured to generate a $B_0$ magnetic field in the bore, and wherein the local shim coil is configured to generate the local shimming magnetic field in the bore of the MRI scanner.

17. The MRI system according to claim 14, further comprising:
a local shim power supply that is configured to provide a direct current (DC) to the local shim coil so that the local shim coil generates the local shimming magnetic field.

18. The MRI system of claim 14, wherein the continuous conductor has a first portion at a first half of the local shim coil between the first side of the housing and the center of the length, and further has a second portion at a second half of the local shim coil between the second side of the housing and the center, and wherein the first portion and the second portion mirror each other.

19. The MRI system according to claim 14, wherein the plurality of sets of loops respectively form a plurality of spiral-shaped windings wound so the continuous conductor has a greater density adjacent to the center of the length than at the first and second sides.

20. The MRI system of claim 19, wherein the plurality of spiral-shaped windings comprises a first spiral-shaped winding and a second spiral-shaped bordering and respectively on opposite sides of the center of the length, and wherein the plurality of spiral-shaped windings comprises a third spiral-shaped winding and a fourth spiral-shaped winding respectively at the first and second sides of the housing, between which the first and second spiral-shaped windings are arranged, and into which the first and second spiral-shaped windings are laterally and respectively recessed.

* * * * *